United States Patent
Schlossman et al.

(10) Patent No.: US 9,226,880 B2
(45) Date of Patent: *Jan. 5, 2016

(54) ZINC OXIDE POWDER BLENDS, THEIR PRODUCTION AND USE

(71) Applicant: Kobo Products Inc., South Plainfield, NJ (US)

(72) Inventors: David Schlossman, Short Hills, NJ (US); Yun Shao, Belle Mead, NJ (US)

(73) Assignee: KOBO PRODUCTS INC., South Plainfield, NJ (US)

( * ) Notice: Subject to any disclaimer, the term of this patent is extended or adjusted under 35 U.S.C. 154(b) by 35 days.

This patent is subject to a terminal disclaimer.

(21) Appl. No.: 13/775,237

(22) Filed: Feb. 24, 2013

(65) Prior Publication Data

US 2013/0164357 A1    Jun. 27, 2013

Related U.S. Application Data

(62) Division of application No. 12/302,772, filed as application No. PCT/US2006/041417 on Oct. 23, 2006, now Pat. No. 8,383,087.

(51) Int. Cl.
*A61K 8/27* (2006.01)
*A61Q 17/04* (2006.01)
*B82Y 5/00* (2011.01)
*A61K 8/29* (2006.01)
*A61K 8/02* (2006.01)

(52) U.S. Cl.
CPC .............. *A61K 8/29* (2013.01); *A61K 8/0241* (2013.01); *A61K 8/27* (2013.01); *A61Q 17/04* (2013.01); *B82Y 5/00* (2013.01); *A61K 2800/262* (2013.01); *A61K 2800/413* (2013.01); *Y10T 428/2982* (2015.01)

(58) Field of Classification Search
USPC ................................... 424/59, 401
See application file for complete search history.

(56) References Cited

U.S. PATENT DOCUMENTS

2006/0167138 A1* 7/2006 Ishii et al. ............. 523/200

* cited by examiner

*Primary Examiner* — Gina Justice
(74) *Attorney, Agent, or Firm* — Handal & Morofsky LLC

(57) ABSTRACT

This disclosure provides sunscreen products that contain metal oxide powders having discrete size distributions. Metal oxide powders include, for example, zinc oxide and titanium dioxide. Sunscreen products made in accordance with the principles of this disclosure contain metal oxide powders having primary particle sizes of about 10-30 ran and about 50-200 nm.

8 Claims, 2 Drawing Sheets

ZINC OXIDE POWDER BLENDS, THEIR PRODUCTION AND USE

CROSS-REFERENCE TO RELATED APPLICATIONS

This application claims benefit of U.S. Provisional Application 60/729,266, filed Oct. 21, 2005, hereby incorporated by reference.

FIELD OF THE INVENTION

This invention generally relates to sunscreen products that attenuate UVA and UVB radiation. Specifically, sunscreen products of the invention contain blends of discrete particle sizes of ZnO and/or $TiO_2$ to effect the desired attenuation.

BACKGROUND OF THE INVENTION

Awareness of the risks and prevalence of UV-induced skin cancer and consciousness of the damaging cosmetic effects of ultraviolet radiation have fostered recognition in recent years of the desirability of avoiding or controlling the physiological damage wrought by harmful ultraviolet radiation, especially solar ultraviolet. UVC radiation is generally not problematic as little if any penetrates the atmosphere, but may be hazardous if artificial sources such as germicidal lamps or high or low pressure mercury arc lamps are employed.

In contrast to the UVC waveband which is filtered out, both UVA and UVB radiation reach the earth's surface from the sun and may be harmful. Longer wavelength ultraviolet rays in the UVA region, adjacent the visible spectrum, which reportedly constitute 99% of the UV energy reaching the earth's surface, are considered to be the primary cause of tanning but to cause little burning. However, in the longer term UVA rays are also believed responsible for skin aging, causing blotching, freckling, wrinkling and comparable problems. Ultraviolet radiation in the shorter wavelength UVB region of from 290 to 320 nm, though comprising only about 1% of the UV energy is considered more significant in causing burning. Accordingly, protection against UVB radiation has traditionally been a primary target of sunscreen formulation. More recently, there has been a recognition of the desirability of also protecting against UVA radiation to reduce long term skin deterioration.

More seriously, both the UVA and UVB wavebands may be implicated in skin cancers including dangerous melanomas. Skin cancer is by far the most prevalent of all cancers and the incidence in the US is increasing rapidly. For these and other reasons, consistent use of a topical sunscreen is now strongly recommended and is widespread. In light of this need, the art contains many proposals for sunscreen agents and compositions intended to provide protection from damaging ultraviolet radiation.

A wide variety of UV-protective agents suitable for topical application in creams, sprays, lotions and the like is known and has been used in sunscreens. However, most such agents are organic chemicals that are prone to photodegradation and may cross-react with other components of desirable topical formulations. Furthermore, being absorbable into the skin, organic sunscreens may irritate the skin or cause other dermatological or allergenic problems. The art also contains proposals for broad spectrum UV protection.

For example, Deckner U.S. Pat. No. 5,783,174 describes sunscreen compositions intended to provide broad protection in both the UVA and UVB regions which compositions combine a UVA-absorbing dibenzoylmethane sunscreen with a UVB-absorbing benzylidene camphor sunscreen. This composition is intended to avoid problems of photochemical instability attributable, according to Deckner, to photoinduced interaction between dibenzoylmethane and the widely used UVB absorber octylmethoxy cinnamate.

A more recent demand for both higher SPF ("sun protection factor") values and for broad-spectrum protection, has led manufacturers to combine several different organic chemical ingredients, aggravating potential problems of photo-induced cross reactivity. To overcome this problem, Lapidot, et al. describe in U.S. Pat. No. 6,436,375 a method for microencapsulating at least one of two or more active sunscreen ingredients which are photo-unstable when formulated together. The active ingredients can be selected for UVA and UVB activity and can be encapsulated in separate sol-gel microcapsules. A drawback of Lapidot et al.'s proposal is that even if problems of cross-reactivity and photodegradation can be overcome, which may or may not be the case, Lapidot et al.'s method still requires use of active organic sunscreen agents which may be harmful or irritating when absorbed. Furthermore, use of sol-gel microcapsules adds complexity and expense and may be undesirable in some topical formulations. Such microcapsules may also raise issues of dispersibility and compatibility with other ingredients of end product formulations.

There is accordingly a need for a UV-protective agent having broad spectrum activity against harmful solar radiation and which does not depend upon organic chemicals. In light of the problems with organic materials, the suitability of inorganic materials may be considered. Several commercially useful inorganic UV-protective agents are known, notably titanium dioxide, zinc oxide and iron oxide. Iron oxides, however are usually colored or black and therefore have rather limited use in sunscreen applications. Also, they may not be approved for use as sunscreens by regulatory authorities such as the US FDA.

Thus, considerable difficulties face a formulator or other worker seeking broad spectrum UV-protective agents that will be satisfactory for widespread commercial use in a full range of topical commercial products.

Elsom et al. (WO 90/11067) provide single-species metal oxide sunscreen compositions. Specifically provided are sunscreen compositions containing blends of titanium dioxide powders having a particle size of 1-100 nm.

Likewise, Cowie et al. U.S. Pat. No. 4,927,464 also provides single-species titanium dioxide compositions for absorbing UV radiation. Cowie et al. use acicular titanium dioxide wherein the length of the longest dimension is 10-150 nm and the particles are coated with a mixture of alumina and silica.

Iwaya U.S. Pat. No. 5,032,090 suggests use of a combination of titanium dioxide and zinc oxide in anti-suntan cosmetic compositions to block ultraviolet rays in both the UVB and UVA regions. One drawback of this approach is that titanium dioxide may undesirably whiten or blue the skin in some formulations. Also the use of multiple metal oxides having significant reactivity in many sunscreen systems may complicate the issues a formulator of compositions for human topical application must address. Furthermore, although titanium dioxide is approved by regulatory agencies for many UV-protective applications, it is not approved for use in combination with avobenzone, a popular organic sunscreen agent. In addition, titanium is not naturally present in human and other organisms, and may therefore be an undesired ingredient for some prospective users.

Iwaya U.S. Pat. No. 5,032,090 suggests use of a combination of titanium dioxide and zinc oxide with a primary particle size great than 70 nm to 300 nm in anti-suntan cosmetic compositions to block ultraviolet rays in both the UVB and UVA regions. The primary particle size of the zinc oxide claimed is too large to be effective in UVB.

Other formulations of the prior art use single-species zinc oxide compositions for UV absorption. For example, Kobayashi Kose Co. JP 60-231607 provides anti-suntan cosmetics containing 10-30% zinc oxide having a particle diameter of <100 nm.

Mitchell et al. U.S. Pat. No. 5,587,148 discloses sunscreen products intended to absorb both UVA and UVB radiation while providing a clear appearance on the skin. One embodiment of Mitchell et al.'s disclosure employs micronized particles of zinc oxide having a size up to about 0.2 µm and having what are purportedly reduced levels of toxic heavy metals, which are formulated with a liquid carrier into a colorless emulsion. According to Mitchell et al., this formulation "is capable of absorbing a substantial quantity, if not all, of the UV radiation to which the user is exposed." (Column 7, lines 15-17.) However, the Mitchell et al. specification provides little, if any, support for this conclusion. Other distinct embodiments proposed by Mitchell et al. include: use of large crystals of zinc oxide, measuring between about 1-100 microns in diameter; and use of transparent plastic spheres measuring between about 0.01-100 microns in diameter which incorporate a UV-absorbing additive.

Cole et al. U.S. Pat. No. 5,340,567 provides sunscreen products intended for UV absorbance. Cole et al. provide mixed metal oxide compositions containing titanium dioxide having a particle size of less than about 35 nm and zinc oxide having a particle size of less than about 50 nm. The metal oxide particles used by Cole et al. are each of a single substantially uniform size.

A disclosure by inventors herein Yun Shao and David Schlossman, "Effect of Particle Size on Performance of Physical Sunscreen formulas" PCIA conference, Shanghai, China R. P. (1999) ("Shao et al. 1999" hereinafter) and available, at the date of this application, describes some of the effects of size, surface treatment, dispersion vehicle, dispersant and other factors on the UV-protective performance of inorganic sunscreens, notably titanium dioxide and zinc oxide. Shao et al. 1999 emphasize the importance of studying size reduction and the relationship between particle size and performance.

Shao et al. 1999 describe use of dispersions, or "pre-dispersions" of titanium dioxide and zinc oxide, intended for formulation with other ingredients to provide useful end product. Shao et al. 1999 concluded at that time that a high loading of solids in the dispersion were important to size reduction and that other factors should also be considered, including pigment selection, surface treatment, vehicle and dispersant. Titanium dioxide is described as providing excellent protection against UVB along with effective UVA protection at a larger size where scattering may contribute significantly. However, such larger sizes may sacrifice some degree of SPF and transparency.

The protection afforded by zinc oxide is considered by Shao et al. 1999 to vary inversely with particle size. Also, zinc oxide is described as providing efficient UVA protection, often with a low SPF. One difficulty these findings present to the worker seeking to provide a broad-spectrum inorganic UV-protective agent suitable for topical application, is that desired sizes of titanium dioxide particles may cause whitening on the skin, as may be understood from FIG. 5 of Shao 1999. (Nor does Shao et al. 1999 describe an adequate zinc oxide formulation.

Another disclosure of inventors, Yun Shao and David Schlossman herein, namely Discovering an Optimum Micropigment for High UV Shielding and Low Skin Whitening, 23rd IFSCC Congress Orlando 2004 ("Shao et al. 2004" hereinafter) describes studies on the UV attenuation of dispersions of titanium dioxide having a primary particle size ("PPS") as small as 15 nm and of zinc oxide as small as 20 nm which studies include studies of their in vivo SPF efficacy. Shao et al. 2004 conclude that size reduction of titanium dioxide and zinc oxide can remarkably improve the appearance of a sunscreen lotion and can improve the SPF in many cases. However, according to Shao et al. 2004, if the size of the titanium dioxide particles is too small, the energy absorption may shift to UVC wavelengths, weakening the attenuation in the UVA and UVB wavebands. Shao et al. 2004 conclude that zinc oxide could provide an effective SPF at (secondary) particle sizes under 130 nm, but "at the cost of UVA protection".

As may be understood from Shao et al. 2004, secondary particle size may often be more important for ultraviolet protection than is the primary particle size, but the primary particle size of the dry powder is often, but not always, a principal factor in determining the secondary particle size in a liquid dispersion. Some of the data described in Shao et al. 2004 shows that secondary size does not always correlate with primary size. The secondary particle size will usually be substantially greater than the primary particle size, possibly as much as five times greater or even more.

In vivo studies reported in boxes 7-9 of Shao et al. 2004 describe several properties of sunscreens employing the described titanium dioxide and zinc oxide dispersions, including the SPF, the SPF per % of active ingredient and, in box 8, the PFA. "PFA" is a measure of the protection afforded against UVA. Desirable values for PFA may be in the range of from about 4 to about 8. Referring to box 8, which addresses the UV protection of zinc oxide dispersions, no PFAs are reported for the first three test samples, reading down Table 7, which are all described as having relatively smaller (secondary) particles sizes, "PS(nm)", of 110 nm or 130 nm. The last three samples are described as having larger (secondary) particles sizes of 228 nm, or greater, and yield PFAs which are in the target range.

Elsom et al. (WO 90/11067) provide sunscreen compositions which comprise a blend of different particle sizes of titanium dioxide. Preferred compositions comprise 10 to 70% of titanium dioxide having a mean primary particle size of about 15 nm and at least one further grade of titanium dioxide having a mean primary particle size of between about 30 nm and about 50 nm. One drawback of this approach is that titanium dioxide may undesirably whiten or blue the skin in some formulations. The compositions are described as substantially transparent, however, because the refractive index of titanium dioxide is 2.6 they are likely to be too whitening when the objective is to obtain an SPF 25 with a UV balance of 4:1.

"Shao et al. 2004" is here described for the sake of completeness in elucidating the background of the present invention. However, it is to be understood that no admission is made regarding the availability of Shao et al. 2004 as a reference in the United States or any other state or region against the claims of the present application.

Thus notwithstanding the foregoing and other proposals in the art, there is a need for improved UV-protective compositions having properties satisfying the various cosmetic and prophylactic needs of the end user as well as the requirements of a cosmetic formulator who must provide appealing, functional products which can be provided to consumers in a satisfactory and aesthetic condition.

SUMMARY OF THE INVENTION

An object of the invention is to provide an inorganic UV-protective composition which can provide broad-spectrum UV protection. A further object is that the UV protective composition be capable of being formulated into end products which have good transparency to visible light on the skin.

Generally, in accordance with the present invention, sunscreen ingredients for cosmetics, suntanning lotion, or the like in both powder and in liquid dispersion form are made from two different sunscreen materials. Each of these two different sunscreen materials is selected for its characteristic of addressing either the UVA or the UVB component of sunlight. In connection with this, it is noted that both of these components will attenuate UVA and UVB, but are, in the context of the multi-mode formulations of the present invention, more effective in addressing either the UVA or the UVB component.

For example, in the case of zinc oxide dispersions, UVB may be attenuated by particles having a secondary particle size between 100 and 150 nm (and preferably between about 110 and about 130 nm), while UVA may be attenuated using secondary particle sizes ranging between about 160 and about 300 nm (preferably about 210 to about 240 nm).

For example, in the case of zinc oxide particles, UVB may be attenuated by particles having a primary particle size between about 10 and about 50 nm (and preferably between about 10 and about 20 nm), while UVA may be attenuated using primary particle sizes ranging between 35 about and about 120 nm (preferably about 35 to about 60 nm).

For example, in the case of titanium dioxide dispersions, UVB may be attenuated by particles having a secondary particle size between about 100 and about 160 nm (and preferably between about 120 and about 140 nm), while UVA may be attenuated using secondary particle sizes ranging between about 140 and about 300 nm (about 150 to about 180 nm).

For example, in the case of titanium dioxide particles, UVB may be attenuated by particles having a primary particle size between about 10 and about 150 nm (and preferably between about 20 and about 50 nm), while UVA may be attenuated using primary particle sizes ranging between about 20 and about 150 nm (preferably about 35 to about 60 nm).

Combinations of UVA targeted powders with UVB targeted powders, in accordance with the present invention may be used in conventional manners as prior art sunscreen powder materials.

In accordance with the present invention, particularly advantageous performance in a sunscreen product, such as a makeup foundation or face powder, can be achieved using the inventive combinations of UVA targeted zinc oxide powders with UVB targeted zinc oxide powders in a combination powder. Such powders, in accordance with the present invention, are employed where sunscreen powders are typically employed in the industry.

Dispersions containing combinations of UVA and UVB targeted materials in accordance with the present invention may be used in the same ways as prior art sunscreen dispersions.

The dispersions and powders of the present invention provide particularly advantageous performance, in terms of UV balance and transparency, because they function Without imparting a bluish tint on the skin.

In accordance with the present invention, particularly advantageous functioning of a sunscreen product, such as sunscreen lotion, can be achieved using the inventive combinations of UVA targeted zinc oxide dispersions with UVB targeted zinc oxide dispersions in a combination dispersions. Such dispersions, in accordance with the present invention, are employed where sunscreen dispersions, such as dispersions on zinc oxide or titanium dioxide, are typically employed in the industry.

A desirable additional object of the invention is to provide an inorganic UV-protective composition capable of being formulated into dispersions which are non-whitening or induce little whitening at high solids loadings. A still further useful object is to provide dispersions containing the inorganic UV-protective composition that avoid or induce little bluing on pigmented skin.

In addition, titanium is not naturally present in human and other organisms, and may therefore be an undesired ingredient for some prospective users.

Other formulations of the prior art use single-species zinc oxide compositions for UV absorption. For example, Kobayashi Kose Co. JP 60-231607 provides anti-suntan cosmetics which may be formulated to contain 10-30% zinc oxide having a particle diameter of 10 to 60 nm and a light scattering particle. Any 30 nm titanium dioxide may be used to scatter light. Formulations made with these compositions, and using the above guidance, many provide a UV balance of 3:1, but the transparency may not be acceptable in some formulations.

Cole et al. U.S. Pat. No. 5,340,567 provides sunscreen products intended for UV absorbance. Cole et al. provide mixed metal oxide compositions containing titanium dioxide having a particle size of less than about 35 nm and zinc oxide having a particle size of less than about 50 nm. The metal oxide particles used by Cole et al. are each of a single substantially uniform size. Like Kose, formulations made with these compositions can provide UV balance of 3:1, but the transparency may not be acceptable for some formulations.

These and other objects can be achieved by one or more embodiments of the invention described herein.

In one aspect, the invention provides a zinc oxide powder composition for UV-protective use comprising a blend of:
 a) an effective proportion of a first zinc oxide powder component having a first particle size selected for the first zinc oxide powder component to attenuate UVA; and
 b) an effective proportion of a second zinc oxide powder component having a second particle size selected for the second zinc oxide powder component to attenuate UVB;
 wherein the mean particle size of the first zinc oxide component is greater than the mean particle size of the second zinc oxide component.

Pursuant to the invention, the relative proportions of the first and second zinc oxide components can be adjusted, or selected, to provide a desired balance of UVA versus UVB protection. For example, the proportion by weight of the first component to the second component may be selected to be in the range of from about 1:2 to about 2:1. Some useful embodiments of the invention employ a proportion by weight of the first component to the second component in the range of from about 1:1.4 to about 1:1.

In another aspect, the invention provides a UV-protective composition comprising an effective amount of a first zinc oxide particulate component having a mean primary particle size in the range of from about 50 to about 200 nm and an effective amount of a second zinc oxide particulate component having a mean primary particle size in the range of from about 10 to about 30 nm. As indicated above, "primary particle size" references the size of the dry, untreated powder.

In a further aspect, the invention provides an UV-protective composition comprising a dispersion in a liquid vehicle of an effective amount of a first zinc oxide particulate component having a mean secondary particle size greater than about 180 nm and an effective amount of a second zinc oxide particulate component having a mean secondary particle size less than about 150 nm. As indicated above, the secondary particle size references the size of the particles in the dispersion. Particle sizes referenced herein are as determined by light scattering analysis, as described hereinafter unless otherwise indicated explicitly or by the context.

Suitable dispersions may employ hydrocarbon or other fluids or oils or silicone fluids as liquid vehicles, although aqueous vehicles may also be used. The dispersions are preferably solids-rich. Usefully, the solids-rich zinc oxide dispersions may employ effective, usually small, proportions of chemical dispersing agents, or dispersants, as is known to those skilled in the art. Also the zinc oxide particles may be coated to enhance their dispersibility, as is also known in the art.

Alternatively, the formulator may incorporate the zinc oxide powder blend, in powder form, with other suitable ingredients to prepare a final product. As a further alternative the zinc oxide powder components, rather than being pre-blended may be separately added.

The two zinc oxide components can be supplied for incorporation into the UV-protective product as a particulate or powder blend or may be separately added to one or more other ingredients to provide the UV-protective composition. Some process embodiments of the invention include steps of blending the two or more dry zinc oxide powder ingredients together and adding the blend to other ingredients. Pursuant to the invention it is believed that, in end product formulations, the first and larger zinc oxide component can provide useful UVA protection and the second and smaller zinc oxide component can provide useful UVB protection.

The first zinc oxide powder component can have a mean primary particle size in the range of from about 50 to about 200 nm to provide UVA protection. In one embodiment of the invention the primary particle size of the first zinc oxide component is in the range of from about 60 to about 100 nm.

The second zinc oxide powder component can have a mean primary particle size in the range of from about 10 to about 30 nm to provide UVB protection. In another embodiment of the invention the primary particle size of the second zinc oxide component is about 20 nm.

The invention includes embodiments employing combinations of the mean particle sizes of the first and second components. For example one tranche of zinc oxide particles having a mean size in the range of about 50 to about 200 nm may be combined with another tranche of zinc oxide particles having a mean size in the range of about 10 to about 30 nm. In another example, particles of about 60 to about 100 nm of the first component may be combined with particles of size of about 20 nm of the second component.

In another aspect, this invention provides a sunscreen product comprising a dispersion of a first zinc oxide powder having a first primary particle size and capable of attenuating ultraviolet radiation, and a second zinc oxide powder having a second primary particle size and capable of attenuating ultraviolet radiation, wherein the first and second primary particle sizes provides a bimodal particle size distribution and wherein the sunscreen product is substantially transparent to visible light.

In another aspect, this invention provides a sunscreen product comprising a dispersion of a first metal oxide powder having a first primary particle size of less than 30 nm and a second metal oxide powder having a second primary particle size of 50-260 nm, and wherein said sunscreen product is substantially transparent to visible light.

In one embodiment, both the first and the second metal oxide powders are zinc oxide. Alternatively, the metal oxides are zinc oxide and titanium dioxide.

In useful embodiments of any of the foregoing aspects, the first primary particle size is less than 30 nm (e.g., between about 10 nm and about 30 nm) and the second primary particle size is between about 50 nm and about 250 nm. In another embodiment, the second primary particle size is greater than 60 nm. Other useful sunscreen products have an average secondary particle size of greater than about 200 nm.

In other embodiments, the ratio by weight of the first metal oxide powder to the second metal oxide powder is about 1:3 to about 3:1, or about 1:1.6 to about 1:1.

In some embodiments, the sunscreen products provide an SPF of at least 30 and/or a PA of at least 10. Desirably, the SPF:PA ratio is at least about 3:1.

In other formulations, the sunscreen products further comprise a third metal oxide powder (e.g., ZnO or $TiO_2$) having a third primary particle size (e.g., between about 10 nm and about 30 nm).

Desirably, the total amount of metal oxide powders in the sunscreen products is less than about 50% or even less than about 25%.

The metal oxide powders may, individually, be uncoated, coated with another metal oxide coating (e.g., alumina and/or silica), a hydrophobic surface treatment (e.g., a polysiloxane), or a hydrophilic surface treatment.

Optionally, the sunscreen products may further comprise a dispersing agent, a color pigment, and/or an organic sunscreen agent.

In another aspect, the invention provides a cosmetic product comprising any sunscreen product made in accordance with the principles of this disclosure, along with a color pigment (e.g., iron oxide).

The invention also includes processes of preparing the novel UV-protective compositions described herein, end product, intermediate and other formulations containing or comprising the novel UV-protective compositions and processes for preparing such formulations.

The ultraviolet ("UV" herein) region of the electromagnetic spectrum comprises three wavebands, designated UVA from 320 to 400 nm, UVB from 290 to 320 nm and UVC from 200 to 290 nm. The UVA band can be further divided into UVAI from 320 to 340 nm and UVAII from 340 to 400 nm. The visible portion of the spectrum is generally from about 400 to about 700 nm. Natural sunlight is a potent source of UV radiation. UV radiation may compose about 10 percent of the solar radiation reaching the earth's surface and is well recognized as the cause of serious biological damage to humans and other animals.

By "substantially transparent to visible light", when referring to a sunscreen product, is meant a product that has an E310/E524 ratio of at least 10, but preferably 15, 20, 25, or more.

In this specification, "primary particle size" may be understood to reference an average or mean particle size of the metal oxide as a dry powder. This primary particle size is established during the manufacture process.

The "secondary particle size" or "secondary agglomerate size" refers to the size of particle aggregates that form in a formulation and cannot be broken up by the dispersion process. The secondary particle size is typically about 100-200 nm, but may vary outside of that range for specific formulations.

"Large agglomerates" include, for example, powders that form as a result of van der Wahl forces and are typically about 0.2-5.0 μm.

DETAILED DESCRIPTION OF THE INVENTION

Figure 1A:
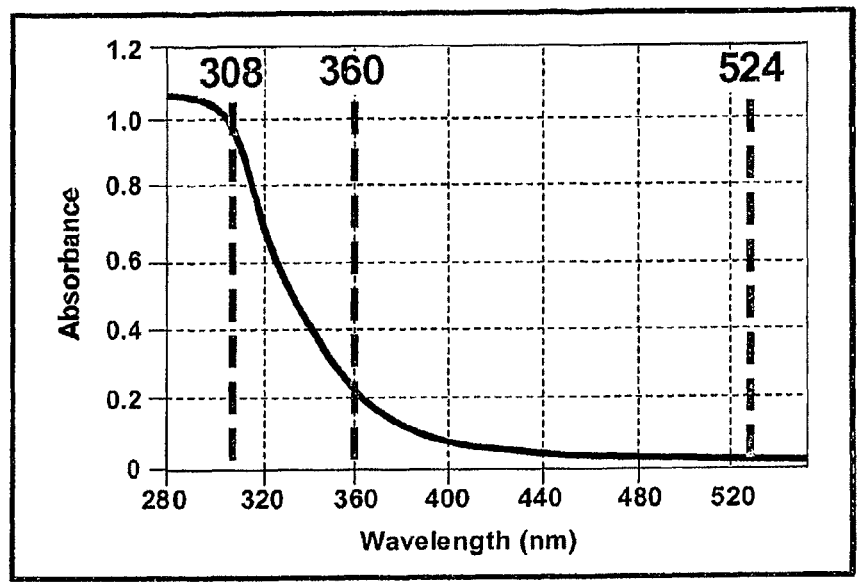
FIG. 1 is a series of graphs illustrating the absorbance of light as a function of wavelength for titanium dioxide (A) and zinc oxide (B).

Some embodiments of the invention, and of making and using the invention, as well as the best mode contemplated of carrying out the invention, are described in detail below. The following more detailed description of the invention is intended to be read as a whole with the preceding summary and background descriptions which may also include pertinent description of the invention, the scope of application of the invention or of elements of the invention, as will be apparent to those skilled in the art, in light of this specification when read as a whole.

The present invention provides novel inorganic compositions of particulate, i.e. powdered, UV-protective ingredients that have broad spectrum activity and provide useful absorption and/or scattering in both the UVA and UVB wavebands of the solar energy received at the earth's surface.

The present invention is in contrast to prior art formulations, such as that shown in Cowie et al. U.S. Pat. No. 4,927,464, discloses titanium dioxide particulates for attenuating UV radiation. Cowie et al. use acicular titanium dioxide wherein the length of the longest dimension is reported between 10-150 nm and the particles are coated with a mixture of alumina and silica. These particles and also oil dispersions containing these particles will be too whitening to make an SPF formulation with a UV balance of 4:1, because of the high refractive index of titanium dioxide. For example, rutile titanium dioxide has an index of refraction of about 2.76 and anatase titanium dioxide has a refractive index of 2.52. In contrast, zinc oxide has an index of refraction of about 1.9. By "UV balance" in this specification is meant the ratio of sun protection factor (SPF) to protection against UVA (PA). Current thinking is that the UV balance should be in excess of 3:1.

In one embodiment, the inventive compositions comprise first and second zinc oxide powder components having particle sizes, or size distributions chosen to selectively attenuate, by absorption, scattering or both absorption and scattering, the UVA and UVB wavebands respectively. For example, the one component may have relatively larger particles to selectively absorb UVA and the other component may have relatively smaller particles to selectively absorb UVB. Desirably, the two zinc oxide powder components can be formulated into compositions, such as dispersions, which are transparent when topically applied, for which purpose relatively small, submicron sized particles may be employed.

UV-protective agents are agents which help or are intended to help protect organisms, especially humans and other susceptible animals, from the harmful effects of UV radiation, notably, without being so limited, solar radiation at the earth's surface. Typically, although not exclusively, such protection is obtained by topical application to the skin and other surfaces of compositions formulated with suitable, protective proportions of one or more UV-protective agents. It will be understood that compositions, including compositions described herein, which effectively protect human skin, may have other useful protective functions e.g. in industrial coatings, plastics or other products.

The first zinc oxide component can be selected to provide an attenuation peak in the UVA waveband, by absorption and/or scattering of the radiation which attenuation peak is useful in preventing the harmful effects of UVA radiation. Comparably, the second zinc oxide component can be selected to provide an attenuation peak in the UVB waveband, by absorption and/or scattering of the radiation which is useful in preventing the harmful effects of UVB radiation. Such a combination of components can provide effective broad-spectrum protection against the UV components of atmospherically filtered solar radiation.

The inventive zinc oxide powder blends are to be understood to include not only dry physical admixtures of the two defined zinc oxide powder components but also other combination these two zinc oxide powder components, for example dispersions of the two components in a liquid vehicle, which dispersions are formed by separate addition of the individual zinc oxide powder components to the liquid vehicle. End products, or intermediate products, which are themselves powder blends, or largely comprise powder blends, can also comprise the individually added or blended zinc oxide components.

The invention provides compositions comprising relatively simple ingredient mixtures that are attractive to a cosmetics formulator to use in preparing formulations for topical application. Such formulations may include, without limitation, sunscreen oils, creams, lotions and the like, and other cosmetic, dermatologic, pharmaceutical or medicament compositions for topical or other use. One object fulfilled by the invention is to provide beneficial UV-protective compositions which avoid presenting new challenges or concerns to a cosmetics formulator. Another is to provide the formulator easy-to-use UV-protective compositions which can readily be incorporated not only in topical sunscreen products to provide protection against acute exposure, but also in other cosmetic products including, without limitation, products such as lipsticks and lip balms, makeups, nail polishes, hair treatments, and so on, to provide everyday protection.

Modern cosmetics compositions are complex, and may include a variety of active ingredients to improve rather than merely mask the appearance and/or condition of the skin. Examples of such actives include low molecular weight alpha- and beta-hydroxy acids, ceramides, cerebrosides, antioxidants, phytoceuticals and a wide variety of other compounds. End products are required to meet ever higher safety and performance standards and to survive long shelf lives under a variety of conditions, after which such products are expected to have flawless esthetic qualities of appearance, feel and aroma, and to perform their intended functions.

With these objectives in mind, the formulator may be faced with the daunting challenge of assessing not only the individual safety and efficacy of a long list of ingredients under various conditions, but also that of determining whether adverse cross-reactivity or other interactions may occur. For these understandable reasons, the formulator may be reluctant to employ unfamiliar or untried ingredients or combinations of ingredients that do not have a long history of safe and effective use. The compositions of the present invention avoid these problems by providing novel UV-protective compositions which employ active ingredients that are known to be safe and effective and have a long history of satisfactory use in a wide variety of cosmetic and other formulations.

Toward these ends, the invention provides an inorganic UV-protective composition comprising a blend of two or more zinc oxide powder components having different size characteristics. Desirably, one component has a significantly greater mean particle size than the other, for example a difference in the range of from about 20 nm to about 50 nm, or greater. The size characteristics beneficially can be selected to provide UV protection in different parts of the UV spectrum so that the blend provides good broad spectrum UV protection. However, characteristics other than size may be employed to provide differential wavelength-related protection, for example, different chemical or physical treatment of the particles in one component from another, or differences in coating characteristics.

The differential protective properties of the two components may comprise differences in absorption of UV energy or of scattering of UV energy or of a combination of absorption and scattering. These differences may occur at different wavelengths or wavebands of the UV spectrum or other useful location in the electromagnetic spectrum which is helpful in protecting human or other animals from received radiation that may be damaging. The invention includes embodiments wherein the protective properties are identifiable as being associated with extinction maxima or with peaks of absorption and/or scattering in the electromagnetic spectrum provided by the UV-protective agents employed.

It will be understood that the properties of the zinc oxide powder components of interest will usually be the properties provided by the material in an end product topical composition where the powder particles may be present in aggregates and/or agglomerations, as opposed to properties that might be displayed in upstream compositions or starting compounds where smaller particle structures may prevail.

In liquid or solid dispersions or blends in which zinc oxide particles are often incorporated, the mean size of the bulk particles that are generally formed after processing and mixing with other ingredients may be significantly larger than the primary particle size of the dry zinc oxide powder after milling, for example up to about 2 to about 5 times larger, or more, as is described in Shao et al. 1999. Smaller primary particles may aggregate, or agglomerate more than do larger particles. This mean size of the bulk particles may be termed the "secondary particle size". The UV protective properties of the end product formulation will often relate to the secondary particle size and the secondary particle size may, in turn, be influenced by the coating or other surface treatment applied to the zinc oxide particles. Thus, the protective properties afforded by the different zinc oxide components, in some embodiments of the invention, can be varied by employing different surface treatments.

Desirably, each component can be composed of small zinc oxide particles that are transparent to visible light and avoid whitening or bluing of pigmented skin, or otherwise provide an undesired visual effect. In many embodiments, two zinc oxide components are sufficient to provide desired broad-spectrum UV protection. However, the invention also includes embodiments employing three or more zinc oxide components having protective properties with peak effects in different parts of the UV spectrum or in parts of the electromagnetic spectrum closely adjacent to the ultraviolet, if such are determined to be relevant to biological health. The three or more different zinc oxide components can have different UV processing or protective characters, one from another, derived from one or more characteristics such as primary particle size and one or more surface treatments, e.g. inorganic oxide or hydroxide, organic fatty acid, silicone, titanate or other treatments.

If desired for particular purposes, for example for protection from artificial radiation, e.g. provided by a tanning salon or the like, a zinc oxide component that protects against UVC can be included.

In some, but not all, useful embodiments of the invention, the zinc oxide blend comprises first and second zinc oxide powder components having particle sizes selected to provide UVA and UVB protection, respectively. To this end, the first zinc oxide powder component can have a mean primary particle size in the range of from about 50 to about 200 nm. In one embodiment of the invention the primary particle size of the first zinc oxide component is in the range of from about 60 to about 100 nm.

The second zinc oxide powder component can have a mean primary particle size in the range of from about 10 to about 30 nm to provide UVB protection. In further embodiments of the invention the primary particle size of the second zinc oxide powder component is in the range of about 15 to about 25 nm, for example, one particular embodiment of the invention employs a particle size of about 20 nm. The invention includes embodiments wherein the primary particle size of the second zinc oxide powder component is in the range of about 15 to about 25 nm and the primary particle size of the first zinc oxide component is in the range of from about 60 to about 100 nm.

The invention also includes embodiments wherein the first zinc oxide powder component has a mean primary particle size in the range of from about 50 to about 200 nm and the second zinc oxide powder component has a mean primary particle size in the range of from about 10 to about 30 nm without regard to selection for provision of UVA or UVB protection.

Desirably, the mean particle size of the first zinc oxide powder component is significantly larger than that of the second zinc oxide powder component, for example at least about 20 nm up to about 100 nm larger, although greater differences may be useful. In some useful embodiments of the invention the difference is from about 30 nm to about 80 nm.

The particle size distribution within each component can be a more or less Gaussian distribution, or the distribution may be whatever non-Gaussian or modified Gaussian distribution is provided by the method of manufacture and processing of the zinc oxide component. Alternatively, the particle size distribution may be modified to enhance the UV-protective performance of one or each zinc oxide component at a selected wavelength or waveband. For example, unduly large particles may be screened out of either zinc oxide powder component, if desired, to reduce the standard deviation. Other techniques can be employed to reduce the standard deviation, if desired, as is known or becomes known to those skilled in the art.

Relative Proportions of Zinc Oxide Components.

Any suitable proportion of the first zinc oxide component to the second zinc oxide component that provides a desired balance of UV-protective properties can be employed. In many, but not all, embodiments of the invention, a modestly higher proportion of the second smaller zinc oxide component may be employed. For example, the proportion by weight of the larger first component to the second smaller component may be in the range of from about 1:2 to about 2:1, or even from about 1:3 to about 3:1. Some useful embodiments of the invention employ a proportion by weight of the first component to the second component in the range of from about 1:1.4 to about 1:1. The invention includes embodiments wherein the proportion of one zinc oxide component to the other is adjusted to provide the desired relative protection in the respective UVA and UVB wavebands.

By varying the relative proportion of one zinc oxide component to the other, for example the ratio of larger particles in one component to smaller particles in the other, the balance of UVA- to UVB-protective properties can be adjusted or controlled. By appropriate selection of initial ingredient particle size, and control of aggregation and agglomeration, the wavelength or wavebands of peak efficacy can be more or less selected. These capabilities provide a formulator with a wide range of options to tailor their products to current and evolving market needs, which needs can be expected to vary as new scientific and other knowledge is acquired.

Proportion of Zinc Oxide in Solids Dispersions.

The dual component zinc oxide materials of the invention can be dispersed into a suitable lipid, silicone or aqueous liquid vehicle in any desired proportion that will provide a smooth, homogenous dispersion and an effective proportion of zinc oxide for the intended purpose. For example, a proportion of from about 5 to about 90 percent by weight the zinc oxide material, based on the weight of the dispersion, can be employed.

Some useful embodiments of the invention employ a zinc-oxide solids loading, or proportion of at least about 20 percent, desirably at least about 30 percent, by weight, for example a proportion in a range of from about 20 to about 80 percent by weight. Lower proportions containing, for example, up to about 40 percent zinc oxide material, can be useful for direct topical application or other purposes. Higher proportions containing, for example, from about 50 to about 80 percent zinc oxide material, can provide useful "premix" solids-rich dispersions suitable for use by cosmetic, pharmaceutical or other formulators for combining with other ingredients to provide useful consumer or other products, as described herein.

For higher SPF values in the end product, and for other purposes, it may be desirable to use a high proportion of zinc oxide solids in the dispersion, consistent with providing a stable, homogenous, dispersion that has enough fluidity for processing. In other words, a high loading of solids is generally desirable for product efficacy, but a loading which is too high may cause processing difficulties or yield a poor quality product. Some useful embodiments of the invention employ more-or-less the highest loading of zinc oxide which can be obtained in a smooth dispersion that has sufficient fluidity for processing. Such products may have a solids content in the range of from about 40 to about 75 percent by weight of the dispersion.

A high proportion of solids in the liquid dispersion medium can be beneficial to the objectives of the invention, as is described herein. For example, during milling of the dispersion, when milling is employed, a high proportion of solid particles can enhance attrition, causing more collisions between particles and converting more of the input energy to size reduction. In addition, a high proportion of solids provides the resultant dispersion with a high viscosity which may be advantageous, for example helping to control re-agglomeration.

Proportions of Zinc Oxide in End Products.

Any proportion of zinc oxide powder or powder blend, may be employed in end product formulations that is effective for one or more of the purposes described herein may be employed.

For example a desirable proportion of the two-component zinc oxide material of the invention may comprise from about 0.1 percent to about 50 percent by weight of the end product. Desirably, the proportion is from about 1 to about 40 percent by weight. Higher proportions in either of these ranges, for example from about 2 to about 30 percent can be useful in a variety of preparations that function primarily as sunscreens and lower proportions, for example from about 0.1 to about 5 percent by weight can be useful in preparations having other utilities where a lower level of UV protection is considered useful, e.g. everyday cosmetics.

The invention includes embodiments of sunscreen or UV-protective compositions intended for topical application to skin, nail or hair comprising from about 2 to about 25 percent by weight zinc oxide material. One such embodiment, or group of embodiments, has a proportion of zinc oxide material of from about 5 to about 10 percent by weight of the end product. Another employs from about 10 to about 15 percent by weight of zinc oxide material.

Preparation of Dispersions and Formulation into End Products.

Various methods can be employed to prepare the zinc oxide materials of the invention for delivery in a useful form to a cosmetics, pharmaceutical or other formulator, for formulation into UV-protective products useful to consumers or other end users.

For example, a specialist vendor, or other supplier may prepare a solids-rich dispersion of the zinc oxide powder blend in a liquid vehicle for use by a formulator, or possibly for direct topical application. The liquid vehicle in such solids-rich dispersions may comprise a suitable oil, a hydrocarbon, a silicone fluid, an aqueous medium or other useful and suitable liquid medium.

The solids-rich zinc oxide dispersions in oil can for example be prepared by first mixing two or more dry powdered commercially available zinc oxide powder components of desired size with the liquid vehicle, in a homogenizer or blender to break up agglomerates. Suitable zinc oxide materials are available inter alia from Tayca Corp. and Advanced Nanotechnology Ltd., (Welshpool, Western Australia). Suitable oils include, for example, isononyl isononanoate, octyl dodecyl neopentanoate and many other oils as are known in the cosmetics, pharmaceutical and other relevant arts. Other suitable liquids include aqueous vehicles and silicone fluids.

The product of mixing, using a high sheer mixer or homogenizer, may be satisfactory, without milling.

However, if desired the dispersion product of the homogenizing or blending process can then be processed in a ball mill or the like to reduce agglomerates and aggregates into smaller particles, continuing milling until a smooth, homogenous dispersion is obtained. The zinc oxide powder components can be added as a powder blend or may be added separately to the liquid vehicle, while mixing, and/or agitating.

Surface Treatments or Coatings.

Usefully, the zinc oxide powder materials may be surface treated to enhance the quality of the dispersion, increase the proportion of solids that can be successfully loaded into the liquid vehicle and thus help provide the end product with a small particle size. If desired, the surface treatment can be selected according to the nature of the intended end product, some options for which are described below.

In one effective embodiment of the invention one or more surface treatment materials, for example a coating agent, is or are blended together with the zinc oxide powder, employing a small quantity of solvent or dispersion vehicle, if needed for workability. This mixture is then heated, while blending or agitating, to a suitable temperature, e.g. from about 110 to about 130° C. and for an appropriate time e.g. from about 2 to about 4 hours or other suitable time period in the range of from about 30 minutes to 24 hours to effect the surface treatment and any associated chemical reaction such as surface bonding, polymerization or cross-reaction. The treated zinc oxide material is mixed into a suitable cosmetic or other liquid vehicle and milled to a fine particle size, for example to the finest size routinely obtainable.

Some suitable surface treatments are described in Shao et al. 1999 and include: use of metal soaps, titanates such as isopropyl titanium triisostearate or lecithin or the like to provide the treated zinc oxide particles with lipophilic properties; use of various silicone materials such as methicone, dimethicone and multifunctional reactive silanes, e.g. triethoxy caprylylsilane to provide hydrophobic properties; and use of reactive fluorinated compounds such as fluoroalcohol phosphate to provide both lipophobic and hydrophobic properties.

Other materials can be used for surface coating as known to those skilled in the art, or as becomes known as the art develops. Some such useful coatings, coated zinc oxide materials and formulations embodying same are disclosed in U.S. Patent Publications Nos.: 2005/0037041 "Duplex coated color lake and other powders, their preparation and cosmetic and other uses"; U.S. 2004/0234613 "Hybrid coated cosmetic powders and methods of making and using same"; and U.S. 2003/0161805 "Organosilicon treated cosmetic powders, their production and use"; each of which patent publications has at least one inventor in common with the present application and are commonly owned with the present application at the date hereof. The disclosure of each of said patent publications is hereby incorporated herein by this specific reference thereto.

Dispersing Agent.

With advantage a dispersing agent or dispersant can be employed in the dispersion to improve dispersion quality, for example PEG 10 dimethicone or acrylates/ethylhexyl acrylate/dimethicone methylacrylate copolymer, or any other suitable dispersing agent as is known or becomes known in the art, some examples of which include polymeric acid amines formed by condensation of a polymeric acid with an amine, for example as described in U.S. Pat. No. 4,349,389 at col. 5, 11. 5-35, the disclosure of which is hereby incorporated herein by reference thereto. The polymeric acid can be a polyester derived from a suitable hydroxy organic acid, for example hydroxystearic acid. The amine employed can be a lower alkylamine, di- or tri-lower alkylamine, or a polyamine for example methylamine, diethylamine, triethylamine, dimethylaminopropylamine, ethylenediame, triethylenetetramine, guanidine or a derivative thereof. Useful dispersing agents include SOLSPERSE (trademark), SOLSPERSE 9000, SOLSPERSE 3000 dispersing agents available from ICI Americas Inc., Wilmington, Del. and the dispersing agents disclosed in U.S. Pat. Nos. 4,349,389, 3,778,287 and 4,157,266. Many other suitable dispersing agents will be known to those skilled in the art, or will become known as the art evolves.

For example, one useful embodiment of the invention employs a polyhydroxystearic acid as a dispersant for an oil, ester or hydrocarbon vehicle. Another embodiment employs castor oil phosphate as a dispersant for such vehicles. For silicone-based dispersions, in silicone fluids, a further embodiment of the invention employs a silicone polyether, for example PEG-10 dimethicone as a dispersant.

Dispersion Analysis.

With advantage, the viscosity and particle size of the resultant dispersion are then determined. Viscosity can be measured using a Brookfield RVT viscometer, or other suitable instrument, after incubating samples at 25° C. for 24 hours. Particle size can be measured by any suitable method. One useful particle size measurement employs a light scattering analyzer, for example a NICOMP 370 photo-correlation particle analyzer. Secondary particle sizes described herein are to be understood to be as determined by such an instrument. Primary particle sizes are as determined and specified by a product supplier. If desired, the primary particle size can be determined or verified by such light scattering analytic methods. As is known in the art, primary particle size can be measured from a SEM (scanning electron micrograph) picture or calculated from the specific surface area.

The formulator, or other party can mix the solids-rich zinc oxide dispersion, produced by the above or other suitable methods, with other ingredients to provide a desired cosmetic, pharmaceutical or other product for topical application. Other suitable ingredients include cosmetic or pharmaceutical vehicles, pharmaceutically or cosmetically active ingredients, excipients, additives, colorants, pigments, perfumes, water and the like, as is known, or becomes known, or apparent in the respective art. Blending, grinding, milling, mixing, heating, agitation, homogenization and other techniques may be employed, as will be understood by these skilled in the art, to combine and process the various ingredients into useful end products.

If desired, and with advantage, in vivo tests can be performed on the sunscreen compositions produced, to determine in vivo values of SPF, optionally using a US FDA, or other suitable protocol. Such in vivo tests can also be used to determine appearance, spreadability, aroma, and other aesthetic qualities, if desired.

In another embodiment of this aspect of the invention, the zinc oxide powder blend, or the components thereof is, or are, admixed with other powder ingredients, for example pigments, fillers and so on, to provide a powdered end product, for example make up.

Supplemental Organic Sunscreen Agent.

The invention also provides a UV-protective composition comprising the dual-component zinc oxide material of the invention in combination with an organic sunscreen agent or agents. Usefully, the organic sunscreen agent can be selected to provide protection against UVB radiation, supplementing that provided by the inventive zinc oxide material. Any desired organic UV-protective agent may be employed, as known, or that becomes known, to those skilled in the art, provided it is compatible with zinc oxide and other ingredients employed in the end product.

One example of a suitable organic UV-protective agent that may be employed is octylmethoxy cinnamate (or 2-ethylhexyl p-methoxycinnamate), commonly abbreviated as "OMC". Others include p-aminobenzoic acid, various benzophenones, oxybenzone, avobenzone, salicylates, various other cinnamates and such organic sunscreen or UV-protective agents as are described in Gildenberg U.S. Pat. No. 6,217,852 and in the patents and other publications referenced in Gildenberg. The disclosure of each one of said patents and other publications is hereby incorporated herein by this specific reference thereto.

Some examples of other organic LTV-protective agents that can be employed include octyl salicylate, octocrylene, oxybenzone, 2-ethylhexyl N,N-dimethylaminobenzoate, p-aminobenzoic acid, 2-phenyl-benzamidazole-5-sulfonic acid, homomenthyl salicylate, avobenzone (e.g., Parsol 1789), DEA p-methoxycinnamate, octylmethoxy cinnamate, 4/4'-methoxy-t-butyldibenzoylmethane, 4-isopropyldibenzoylmethane, 3-(4-methylbenzylidene) camphor, 3-benzylidene camphor, 4-N,N-dimethylaminobenzoic acid ester with 2,4-dihydroxybenzophenone, 4-N,N-dimethylaminobenzoic acid ester with 2-hydroxy-4-(2-hydroxyethoxy) benzophenone, 4-N,N-dimethylaminobenzoic acid ester with 4-hydroxydibenzoyl-methane, 4-N,N-dimethylaminobenzoic acid ester with 4-(2-hydroxyethoxy)dibenzoylmethane, 4-N,N-di(2-ethylhexyl)-aminobenzoic acid ester with 2,4-dihydroxybenzophenone, 4-N,N-di(2-ethylhexyl)aminobenzoic acid ester with 4-hydroxydibenzoylmethane, 4-N,N-di (2-ethylhexyl)aminobenzoic acid ester with 4-(2-hydroxyethoxy)dibenzoylmethane, 4-N,N-(2-ethylhexyl) methylaminobenzoic acid ester with 2,4-dihydroxybenzophenone, 4-N,N-(2-hydroxyethoxy) benzophenone, 4-N,N-(2-ethylhexyl)methylaminobenzoic acid ester with 4-hydroxydibenzoylmethane, 4-N,N-(2-ethylhexyl)methylaminobenzoic acid ester with 4-(2-hydroxyethoxy)dibenzoylmethane and mixtures of any two or more of the foregoing organic UV-protective agents.

Any suitable proportion of the organic sunscreen agent can be employed. For example, the quantity, by weight may be somewhat less than the quantity of the inventive zinc oxide material employed, for example, from about 0.1 to about 2 parts organic agent, or agents, per part of zinc oxide material referring to the combined weight of organic agents if more than one is employed. Some useful embodiments of the invention employ from about 0.5 to about 1.2 parts organic agent, or agents, per part of zinc oxide material, one embodiment of which employs about 0.8 parts organic agent, or agents, per part of zinc oxide material.

Benefits.

The novel dual-component zinc oxide powder materials of the present invention, compositions formulated from the dual zinc oxide powders and the related methods described herein, provide a flexible, biocompatible solution to many ultraviolet protection problems. Cosmetic, dermatological, pharmaceutical, veterinary and other formulators are provided with a novel means of affording both UVA and UVB protection with good transparency, biocompatibility and stability, in sunscreens and other products.

The invention provides a simple inorganic composition, or ingredients therefor, useful embodiments of which have good broad-spectrum ultraviolet efficacy, good SPF (sun protection factor) and PFA (protection factor UVA) which is easy to use, attractive to a cosmetics formulator who must consider physical and chemical properties and interactions of a multiplicity of ingredients. Useful embodiments of the invention also provide good transparency enabling end products that provide good protection against sunlight, are non-allergenic and suitable for extended daily wear and which are attractive to a wide range of users by virtue of their freedom from whitening or bluing.

EXAMPLE 1

Optical Properties of Metal Oxide Powders Useful as Sunscreens

Titanium dioxide and zinc oxide absorb/scatter ultraviolet and visible light. The scattering effect is dependent upon the particle size. Larger particles scatter longer wavelengths and the scattering of visible light results in the whitening effect observed for many sunscreen formulations that use relatively large sized metal oxide particles. Maximum scattering occurs when the particle size equals about one half of the wavelength ($\frac{1}{2}\lambda$) and the particles are uniformly dispersed.

A convenient way to express the UVB scattering effect of a metal oxide relative its whitening effect is to use the extinction ratio at 308/524, which is the ratio of extinction coefficients at 308 nm and 524 nm, where extinction coefficient= (absorbance)/(concentration*cell length). These wavelengths are conveniently selected because 308 nm corresponds to the UVB wavelength that has maximum erythemal effectiveness (promotes sunburn) and 524 nm is at the "blue-end" of visible light. This ratio indicates the level of transparency. Likewise, the extinction ratio at 308/360 is and index of the relative UVB versus UVA blocking power. The 360 nm wavelength is selected because it is mid-range UVA. For ZnO, the 308/524 ratio is typically close to 1 but it varies based on titanium dioxide particle size.

Figure 1B:
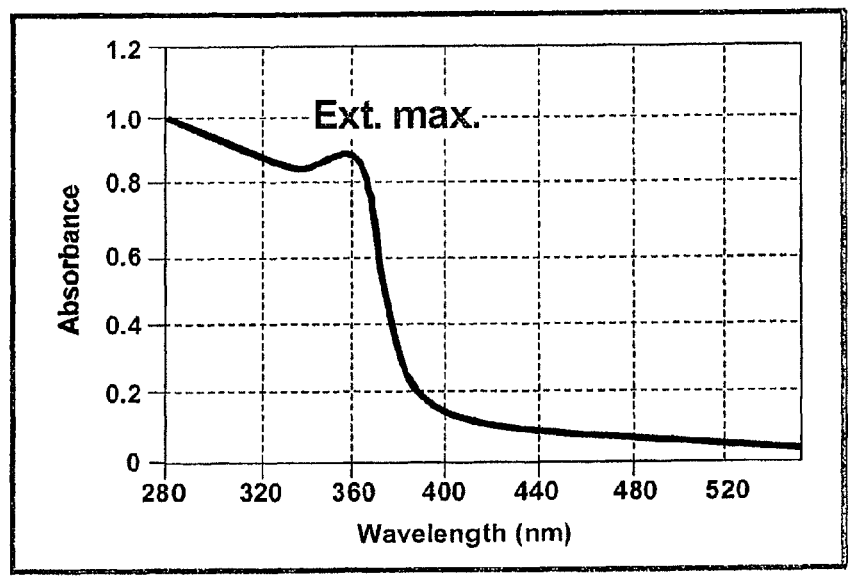

FIG. 1 shows the extinction ratios for titanium dioxide and zinc oxide. While titanium dioxide has the highest extinction in the extreme UVB range, ZnO has amore uniform absorption through the ultraviolet range. Thus, beneficial sunscreens contain a mixture of the two metal oxides.

TABLE 1

Extinction Ratios

| Pigment | Primary Particle Size | Ratio E305/E360 | Ratio E305/E524 | Max. Absorption ($\lambda$) |
|---|---|---|---|---|
| TiO$_2$ | 10 nm | 7.0-8.0 | 70-90 | 275 nm |
| | 15 nm (High Speed Dispersion) | 4.5-5.5 | 50-55 | 280-305 nm |
| | 15 nm (High Solids Dispersion) | 3.4-3.9 | 11-16 | 290-305 nm |
| | 20 nm | 2.0 | 9 | 300 nm |
| | 35 nm | 1.5-2.0 | 7-17 | 315 nm |
| | 150 nm | 1.1 | 2.6 | 318 nm |
| ZnO | 20 nm | 1.0-1.1 | 30-37 | 360 nm |
| | 60-100 nm | 1.1 | 6.3 | 371 nm |
| | 120 nm | 0.9 | 2.9 | 375 nm |

EXAMPLE 2

Comparison of Sunscreen Formulations

Two different metal oxide blends were formulated and compared as follows:

Blend 1. Blend 1 was made using a zinc oxide dispersion sold under catalogue number TNP50ZSI by Kobo Products, Inc. Catalog number TNP50ZSI contains 46.7% ZnO, by weight, having a primary particle size equal to about 20 nm. Blend 1 also incorporated a zinc oxide dispersion sold under catalogue number OHN73MZ by Kobo Products, Inc. Catalogue number OHN73MZ contains 70% ZnO having a primary particle size in the range between 15 and 35 nm.

Blend 1 was formulated to have an SPF of about 30 and protection against UV factor or PA of about 10. Blend 1 contained 19%, by weight, zinc oxide from catalogue number TNP50ZSI, resulting in a final concentration of about 9% ZnO having a 20 nm particle size, and about 21.3% ONH73MZ, resulting in a final concentration of about 15% ZnO in the 15-35 mm primary particle size range. The formulation was brought to 100% volume using Finsolv.

In accordance with preferred embodiment, for both powder and for liquid dispersions, and for zinc oxide as well as titanium dioxide, the preferred ratio of UVA blocking ingredient to UVB blocking ingredient is thus about 5 to 3, or 1.66 to 1. However, acceptable products may be achieved with ratios varying between 2:1 and 1:2.

In accordance with preferred embodiment, for both powder and for liquid dispersions, and for zinc oxide as well as titanium dioxide, the preferred total of UVA blocking ingredient and UVB blocking ingredient should be between 4 and 50 percent by weight and preferably between 10 and 25 percent by weight.

In accordance with preferred embodiment, for both powder and for liquid dispersions, and for zinc oxide as well as titanium dioxide, the preferred range for UVA blocking ingredient is between 1 and 19 percent by weight and preferably 8 and 17 percent by weight, and most preferably 13-17 percent by weight.

In accordance with preferred embodiment, for both powder and for liquid dispersions, and for zinc oxide as well as titanium dioxide, the preferred range for UVB blocking ingredient is between 1 and 19 percent by weight and preferably 6 and 17 percent by weight, and most preferably 7-11 percent by weight.

It is noted in this specification that UVA and UVB targeted sunscreen components all block UVA and UVB components but are referred to as such herein on account of the design objectives that drive their inclusion in the disclosed formulas.

Blend 2. A titanium dioxide dispersion ON60T5L (Kobo Products, Inc.) contains 48.6% titanium dioxide with a primary particle size of about 35 nm. Blend 2 was formulated to have an SPF of about 30 and a PA of about 10. Blend 2 contained 12.3% of catalogue number ON60T5L, resulting in a final concentration of about 6% $TiO_2$ of primary particle size 35 nm. By weight, 21.3% of Blend 2 consisted of zinc in the form of catalogue number ONH73MZ. The formulation was brought to 100% volume using Finsolv.

Figure 2:
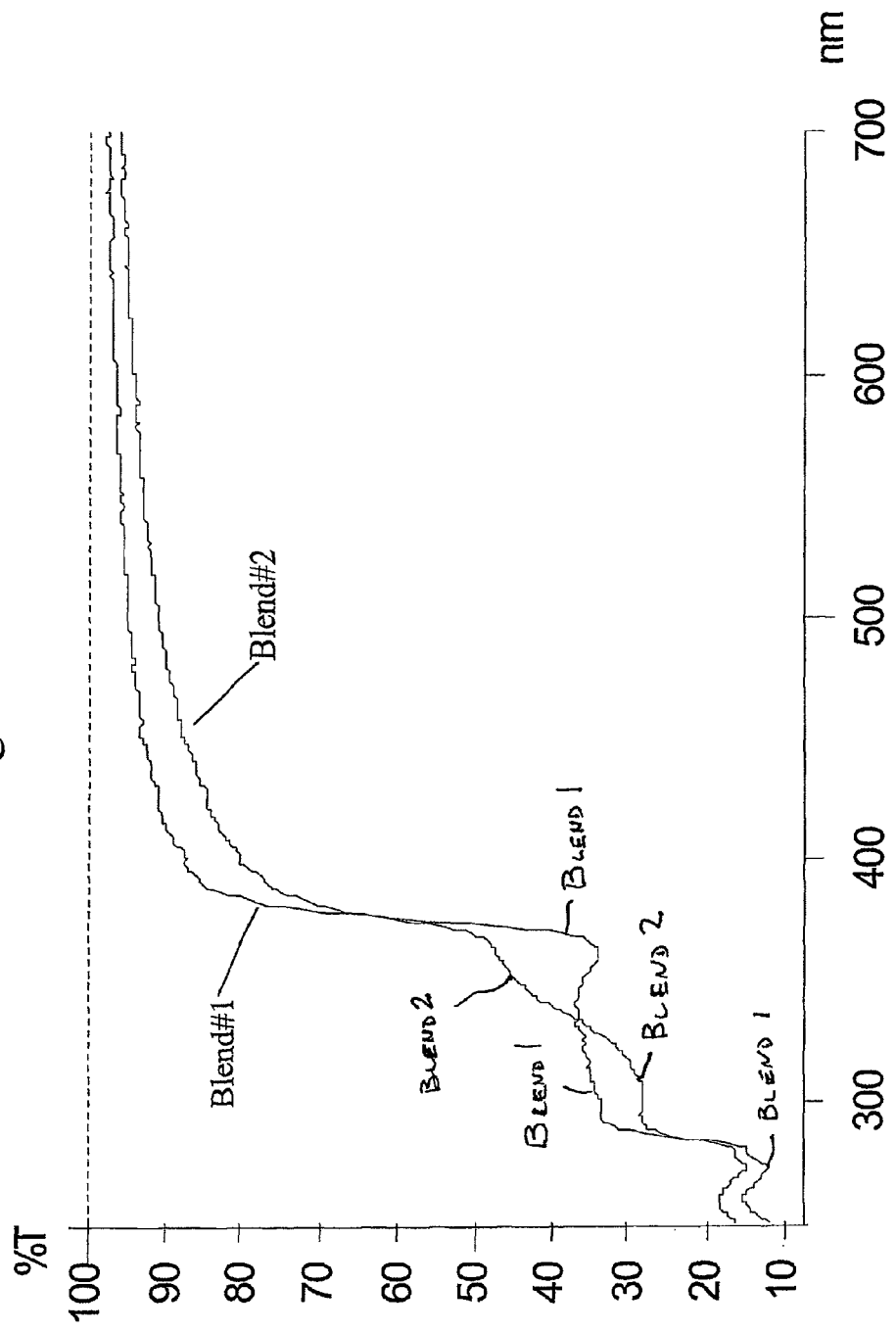
FIG. 2 is a graph showing the relative light transmission of two different sunscreen formulations prepared in accordance with the principles of this disclosure.

Blend 1 and Blend 2 were tested for % light transmittance across the UV and visible spectrum. As shown in FIG. 2, Blend 1 which contains two different ZnO particle sizes provides more balanced UV protection and greater transparency to visible light than Blend 2 which contains zinc oxide and $TiO_2$.

|  | E310/E524 (transparency) | E310/E360 (UVA protection ratio) |
| --- | --- | --- |
| Blend#1 | 22.65 | 0.98 |
| Blend#2 | 15.17 | 1.65 |

Thus, 6% of 35 nm $TiO_2$ provides too much whitening for a skin care product but is useful for other products in which whitening is desired or that are used merely for their protective properties.

The various proportions of ingredients described herein are to be understood to be by weight based on the weight of the relevant composition comprising the ingredient in question, unless the context indicates otherwise.

All publications and patents cited in this specification are herein incorporated by reference as if each individual publication or patent were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A powder sunscreen ingredient for cosmetics, comprising
   (a) as a UVB attenuator, zinc oxide particles having a primary particle size between 10 and 50 nm, and
   (b) as a UVA attenuator, zinc oxide having secondary particle sizes ranging between 35 and 120 nm.

2. A powder sunscreen ingredient for cosmetics as in claim 1, wherein said UVB attenuating zinc oxide particles have a primary particle size between 10 and 20 nm, and said UVA attenuating zinc oxide has a secondary particle sizes ranging between 35 to 60 nm.

3. A dispersion of a powder sunscreen ingredient comprising UVB attenuating zinc oxide particles having a secondary particle size between 110 and 130 nm, and UVA attenuating zinc oxide particles having a secondary particle sizes ranging between 210 to 240 nm.

4. A sunscreen ingredient as in claim 3, wherein said UVB zinc oxide ingredient and said UVA zinc oxide ingredient are selected to have an SPF greater than about 25 and an SPF:PA ratio of at least about 3 measured in vivo.

5. A sunscreen ingredient as in claim 3, wherein said UVB attenuating zinc oxide ingredient and said UVA attenuating zinc oxide ingredient are selected to have an SPF:PA ratio of at least about 3:1.

6. A sunscreen ingredient as in claim 4, wherein said first zinc oxide ingredient is selected to target blockage of the UVA component of sunlight and said second zinc oxide ingredient is selected to target blockage of the UVB component of sunlight.

7. A sunscreen ingredient as in claim 3, wherein the weight ratio of UVA attenuating zinc oxide particles to UVB attenuating zinc oxide particles is between 2:1 and 1:2.

8. A powder sunscreen ingredient comprising a first zinc oxide powder having a first primary particle size and capable of attenuating ultra violet radiation, and a second zinc oxide powder having a second primary particle size and capable of attenuating ultraviolet radiation, wherein said first and second primary particle sizes provide a bimodal particle size distribution and wherein said sunscreen product is transparent to visible light.

* * * * *